United States Patent [19]

Suzuki et al.

[11] Patent Number: 5,417,885
[45] Date of Patent: May 23, 1995

[54] ANTIFERROELECTRIC LIQUID CRYSTAL COMPOUND

[75] Inventors: Yoshiichi Suzuki; Takashi Hagiwara; Ichiro Kawamura, all of Tokyo, Japan

[73] Assignee: Showa Shell Sekiyu Kabushiki Kaisha, Tokyo, Japan

[21] Appl. No.: 101,026

[22] Filed: Aug. 3, 1993

[51] Int. Cl.⁶ .................. C09K 19/12; C09K 19/20; C07C 69/76
[52] U.S. Cl. ............... 252/299.65; 252/299.66; 252/299.67; 560/65
[58] Field of Search ............... 252/299.01, 299.64, 252/299.65, 299.66, 299.67; 560/65

[56] References Cited

U.S. PATENT DOCUMENTS

| | | | |
|---|---|---|---|
| 4,808,333 | 2/1989 | Huynh-Ba et al. | 252/299.66 |
| 4,834,906 | 5/1989 | Coates et al. | 252/299.63 |
| 4,895,671 | 1/1990 | Ushioda et al. | 252/299.61 |
| 5,064,569 | 11/1991 | Geelhaar et al. | 252/299.65 |
| 5,122,295 | 6/1992 | Weber et al. | 252/299.01 |
| 5,214,523 | 5/1993 | Nito et al. | 252/299.01 |

FOREIGN PATENT DOCUMENTS

| | | |
|---|---|---|
| 301511 | 2/1989 | European Pat. Off. |
| 360043 | 3/1990 | European Pat. Off. |
| 0525737 | 2/1993 | European Pat. Off. |
| 64-03154 | 1/1989 | Japan |
| 1-211554 | 8/1989 | Japan |
| 269440 | 3/1990 | Japan |
| 5-17409 | 1/1993 | Japan |
| 5132449 | 5/1993 | Japan |
| 5140042 | 6/1993 | Japan |
| 5140043 | 6/1993 | Japan |
| 2200912 | 8/1988 | United Kingdom |
| WO8908690 | 9/1989 | WIPO |

OTHER PUBLICATIONS

Shigeru et al., "Optically Active Fluoroalkyl Benzoate Derivatives as Liquid Crystals", Chemical Abstracts, vol. 111, No. 4, Jul. 1989, Abstract No. 31747p.

A. Chandani et al., "Antiferroelectric Chiral Smectic Phases . . . ", Jpn. J. Appl. Physics, vol. 28, No. 7, Jul. 1989, pp. L1265-L1268.

N. Miyaura et al., "The Palladium-Catalyzed Cross--Coupling Reaction . . . ", Synthetic Communications, 11(7), pp. 513–519, 1981.

*Primary Examiner*—Shean Wu
*Attorney, Agent, or Firm*—Cushman Darby & Cushman

[57] ABSTRACT

An antiferroelectric liquid crystal compound of the following formulae:

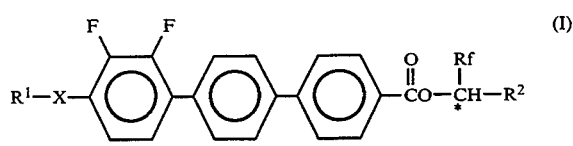

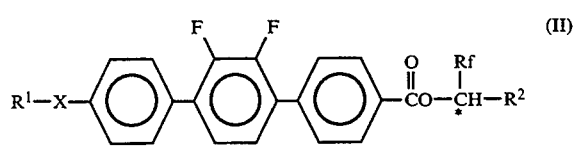

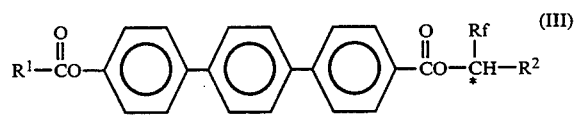

wherein $R^1$ and $R^2$ each is an alkyl group of $C_4$-$C_{18}$, Rf is $CF_3$ or $C_2F_5$, X is O, COO, or a single bond, and * shows an optically active carbon atom.

13 Claims, 8 Drawing Sheets

APPLIED TRIANGULAR WAVE VOLTAGE

OPTICAL RESPONSE OF NEMATIC LIQUID CRYSTAL ON MARKET

OPTICAL RESPONSE OF LIQUID CRYSTAL HAVING IDEAL BISTABLE STATES

OPTICAL RESPONSE OF LIQUID CRYSTAL HAVING TRISTABLE STATES OF PRESENT INVENTION

SWITCHING OF BISTABLE STATES

SWITCHING OF TRISTABLE STATES

ANTIFERROELECTRIC LIQUID CRYSTAL COMPOUND

FIELD OF THE INVENTION

The present invention relates to a novel antiferroelectric liquid crystal compound having a terphenyl structure.

BACKGROUND OF THE INVENTION

Liquid crystals have excellent characteristics from various points of view, namely,
1) they can be operated at a low voltage;
2) they consume only small amount of power;
3) panel type displays can be used; and
4) they are passive type matrixes.

Accordingly, electrooptical apparatuses using nematic liquid crystals such as a DSM cell, TN cell, G-H cell, or STN cell have been developed and practically used. However, all of the electrooptical apparatuses using such nematic liquid crystals have a defect that response time is as slow as several milli sec to several tens milli sec, leading to a restriction in their applications.

In order to solve these problems, active matrix drive systems using STN cells or thin-film transisters were developed. However, STN type displays have problems that a high accuracy is required in controls of cell gap and tilt angle and that response time is rather slow, while they are excellent in such qualities as display contrast and viewing angle.

With such a technical background, the development of a ferroelectric liquid crystal had been attempted which has a spontaneous polarization (Ps), has a strong torque based on $Ps \times E$ (E is an applied voltage), and has an extremely short optical response time of a few $\mu$sec to several tens of $\mu$sec to make the preparation of a hypervelocity device possible.

Meyer et al. synthesized DOBAMBC (p-decyloxy-benzilidene-p-ammino-2-methylbutyl cinnamate) in 1975 for the first time in the world and which was confirmed to be a ferroelectric liquid crystal (Le Journal de Physique, Vol. 36, 1975, L-69).

Further, since Clark and Lagawall reported in 1980 on such characteristics on display devices as high velocity response of submicroseconds and memory characteristics of DOBAMBC, ferroelectric liquid crystals have absorbed considerable public attention (N. A. Clark et al., Appl. Phys. Lett. 36, 899 (1980)).

However, from a practical standpoint, there were many technical problems in that system. In particular, no material exhibited ferroelectric liquid crystallinity at an ambient temperature, and an effective and practical method was not established to control the molecular alignment of the liquid crystal molecules. Controlling the molecular alignment of liquid crystal molecules is essential for applications in liquid crystal devices.

After the publication of the report, various attempts have been made from both aspects of liquid crystal materials and device. Display devices utilizing the switching between twisted bistable states were prepared for trial, and high speed electrooptical apparatuses using the device are proposed in U.S. Pat. No. 4,367,924 and others. However, high contrast and proper potential of threshold value have not been obtained.

From such a point of view, other switching systems were explored to propose a transitional diffusion system. subsequently, a three states switching system of liquid crystal having tristable states was reported in 1988 (A.D. L. Chandani, T. Hagiwara, Y. Suzuki et al., Japanese J. of Appl. Phys., 27, (5), L729–L732 (1988)).

The optically tristable states herein referred to mean that, when voltage in the form of a triangular wave as shown in FIG. 1A is applied to liquid crystal electrooptical devices where antiferroelectric liquid crystals are laid between the first electrode substrate plate and the second electrode substrate plate which is apart at a given space from the first one, the antiferroelectric liquid crystals show the first stable molecular orientation and resulting the first optically stable state as shown in FIG. 3 (a), and FIG. 1(D) at reference point 2, respectively, when electric voltage is zero. The antiferroelectric liquid crystals show the second stable molecular orientation and resulting the second optically stable state as shown in FIG. 3 (b), and FIG. 1(D) at reference point 1, respectively, in one of the direction of electric field; and show the third stable molecular orientation and resulting the third optically stable state as shown in FIG. 3 (c), and FIG. 1(D) at reference point 3, respectively, in the other direction of electric field.

Liquid crystal electrooptical apparatuses utilizing the tristable states, that is three stable states, are proposed in U.S. Pat. No. 5,046,823 filed by the present applicant.

The characteristics of an antiferroelectric liquid crystal showing the tristable states are described in more detail below.

In the ferroelectric liquid crystal element having a stabilized surface which was proposed by Clark-Lagawall, ferroelectric liquid crystal molecules show two stable states in which the molecules are uniformly oriented or aligned in one direction in the phase S*C. The molecules are stabilized in either state depending on the direction of applied electric field as shown in FIG. 2 at (a) and (b), and the state is kept even when the electric field was shut off.

Actually, however, the alignment of the ferroelectric liquid crystal molecules shows twisted two states in which directors of the liquid crystal molecules are twisted or shows a chevron structure in which layers are bent in a doglegged shape. In the chevron layer structure, switching angle becomes small, forming a cause for a low contrast, and which constitute a serious obstacle for its practical use.

On the other hand, in the liquid crystal electrooptical devices, an "anti" ferroelectric liquid crystal molecules are aligned in antiparallel, tilting in opposite direction at every adjoining layer, in the phase $S^*_{(3)}$ showing the tristable states, and thus, the dipoles of the liquid crystal molecules are negating each other. Accordingly, the spontaneous polarization is nullified as a whole. The transmittance of the liquid crystal phase showing such molecular alignment corresponds to reference point 2 in FIG. 1(D).

Further, when a voltage sufficiently higher than a threshold value of (+) or (−) was applied, liquid crystal molecules shown in FIG. 3 at (b) or (c) are tilted in the same direction and aligned in parallel. In this state, the spontaneous polarization is produced since the dipoles are also shifted to the same direction to form a ferroelectric phase, and the transmittance of the liquid crystal phase in that state corresponds to reference points 1 and 3 in FIG. 1(D).

That is, in the phase $S^*_{(3)}$ of the "anti" ferroelectric phase, the "anti" ferroelectric phase at the time of no-electric field and two ferroelectric phases due to the polarity of applied electric field are stabilized, and switching is carried out among tristable states of an "anti" ferroelectric phase and two ferroelectric phases, with a direct current-like threshold value. Based on the change in the alignment of liquid crystal molecules accompanied with the switching, light transmittance is changed while drawing such a double hysteresis as shown in FIG. 4.

One of the characteristics of the present invention is that a memory effect can be realized by applying a bias voltage to the double hysteresis as shown in FIG. 4 at reference point (A) and further applying a pulse voltage.

Moreover, the ferroelectric phase is stretched in terms of its layer by the application of an electric field to form a book-shelf structure. On the other hand, in the "anti" ferroelectric phase at the time of no electric field, an analogous book-shelf structure is formed. Since the layer structure switching due to the application of an electric field gives a dynamic shear to liquid crystal layers, an alignment defect is improved during driving, and thus, a good molecular alignment can be realized.

In the "anti" ferroelectric liquid crystal, since image display is performed by alternatively using both hysteresises of plus side and minus side, after-image phenomenon due to the accumulation of inner electric field based on the spontaneous polarization can be prevented.

As explained above, the "anti" ferroelectric liquid crystal can be said to be a very useful liquid crystal compound having advantages as follows:

1) Hipervelocity response is possible,
2) High contrast and wide viewing angle can be expected, and
3) Excellent alignment characteristics and memory effect can be realized.

Reports are made on the liquid crystal phase of the "anti" ferroelectric liquid crystal showing the tristable states in the following articles:

1) A. D. L. Chandani et al., Japanese J. Appl. Phys., 28, L-1265 (1989), and

2) H. Orihara et al., Japanese J. Appl. Phys., 29, L-333 (1990).

The liquid phase is called "Phase $S^*_{CA}$" (Antiferroelectric Smectic C phase) in association with the "anti" ferroelectric property. The phase is named "phase $S^*_{(3)}$" in the present specification since the liquid crystal phase performs the switching among tristable states.

The liquid crystal compounds which have the "anti" ferroelectric phase $S^*_{(3)}$ showing the tristable states in a phase series are disclosed in Japanese Unexamined Patent Publication No. 1-316367, U.S. Pat. Nos. 5,171,471 and 4,973,738, and European Patent No. 330,491A filed by the present inventors, and in Japanese Unexamined Patent Publication No. 1-213390 filed by Ichihashi et al. Liquid crystal electrooptical devices utilizing the tristable states are proposed in Japanese Unexamined Patent Publication No. 2-40625 and U.S. Pat. No. 5,046,823.

When "anti" ferroelectric liquid crystals are applied for displays, it is difficult to satisfy all of these required performance of characteristics 1) the range of operation temperature,
2) response time,
3) spontaneous polarization, and
4) hysteresis, with a single liquid crystal. Thus, the liquid crystals are usually used as a mixture of ten-odd kinds of liquid crystals.

Particularly, in respect of the required performance 1) above, that is the range of operation temperature, development of "anti" ferroelectric liquid crystals is desired which show a stabilized display performance characteristic at an area of lower temperatures including room temperature. However, "anti" ferroelectric liquid crystals have not yet been found which stably develop "anti" ferroelectric $S^*_{(3)}$ phase at the area of lower temperatures including room temperature and showing a high speed response.

SUMMARY AND OBJECTS OF THE INVENTION

An antiferroelectric liquid crystal compound according to the present invention is represented by the following formulae:

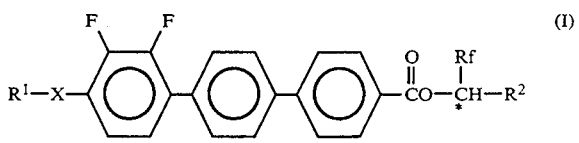

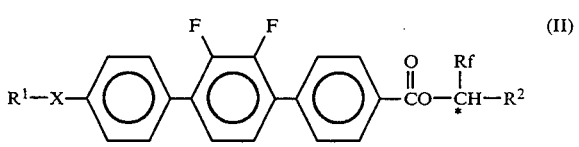

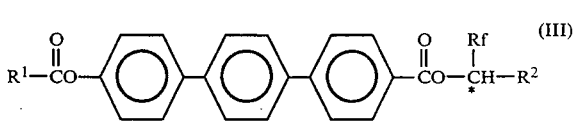

wherein $R^1$ and $R^2$ each is a $C_4$-$C_{18}$ alkyl group, Rf is $CF_3$ or $C_2F_5$, X is O, COO or a single bond, and * identifies an optically active carbon atom.

The object of the present invention is to provide a novel antiferroelectric liquid crystal compound, that is a liquid crystal compound having a phase $S^*_{(3)}$ showing tristable states.

Further object of the present invention is to provide a liquid crystal compound by which a high speed response can be expected and which is very efficient as a component constituting a mixed antiferroelectric liquid crystal.

Still further object of the present invention will be apparent to those skilled in the art from the following detailed description and appended claims.

BRIEF DESCRIPTION OF THE FIGURES

FIG. 4 also shows a bias voltage and a pulse voltage added to the double hysteresis.

DETAILED DESCRIPTION OF THE INVENTION

Figure 1A:
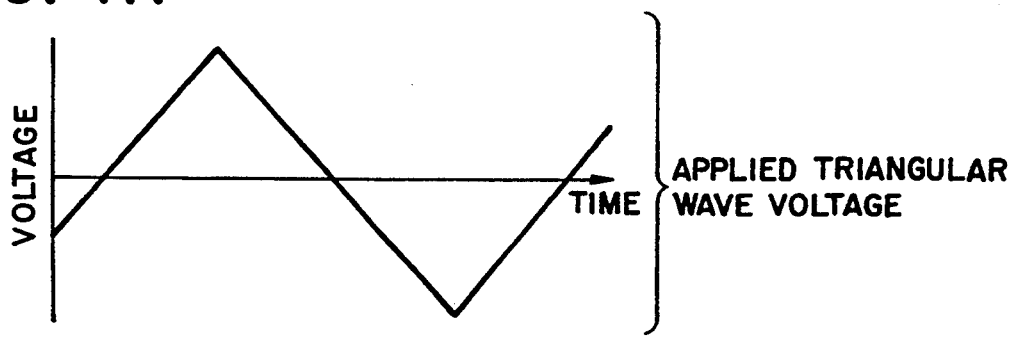
FIG. 1(A) shows an applied triangular wave.
Figure 1B:
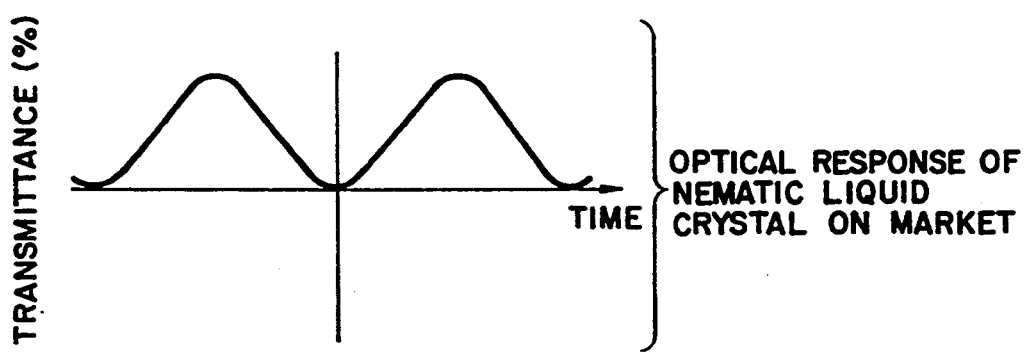
FIG. 1(B), FIG. 1(C), and FIG. 1(D) show the optical response characteristics of a nematic liquid crystal which is on the market, of a liquid crystal showing bistable states and of a liquid crystal showing tristable states, respectively.
Figure 1C:
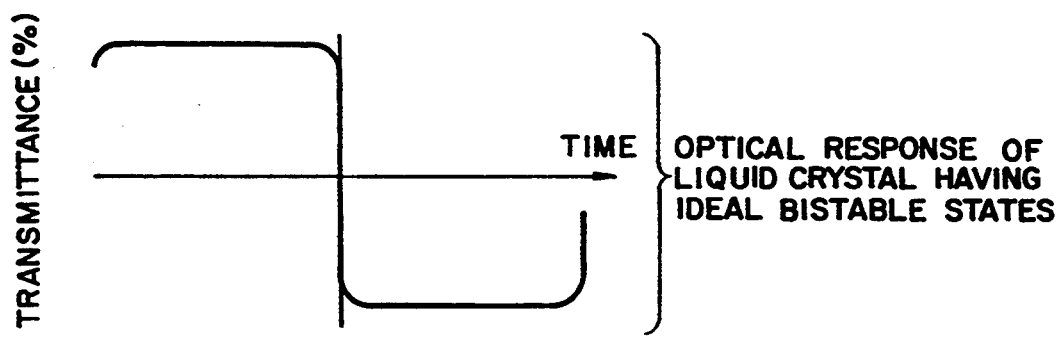
Figure 1D:
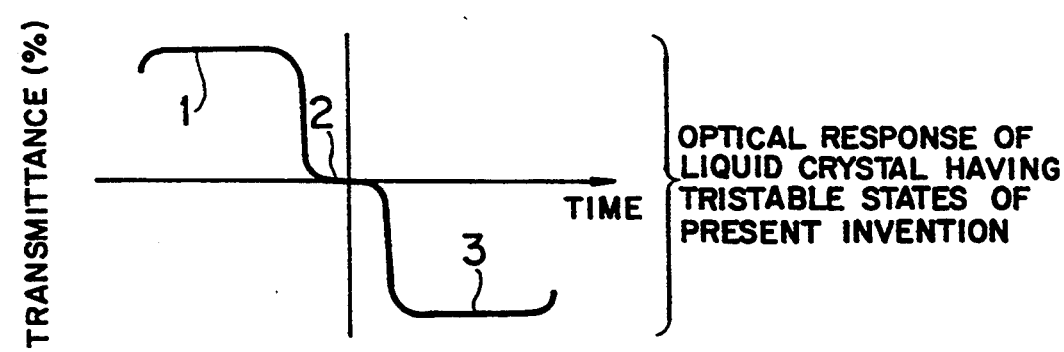
Figure 2:
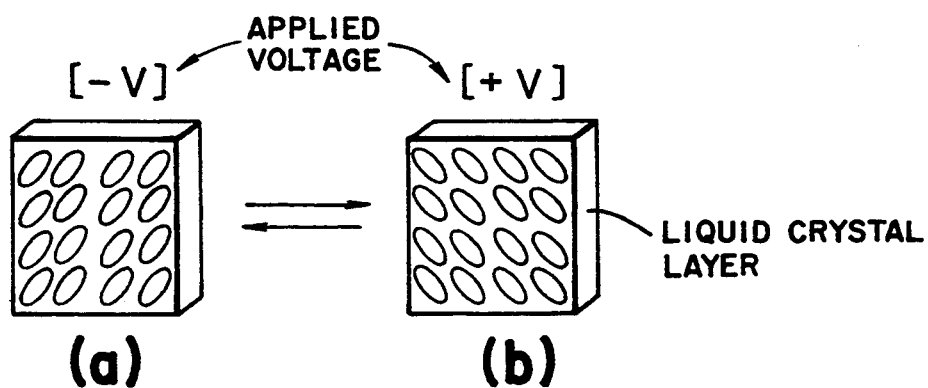
FIG. 2 shows the appearance of aligned ferroelectric liquid crystal molecules in two stabilized states, (A) and (B), proposed by Clark and Lagawall.
Figure 3:
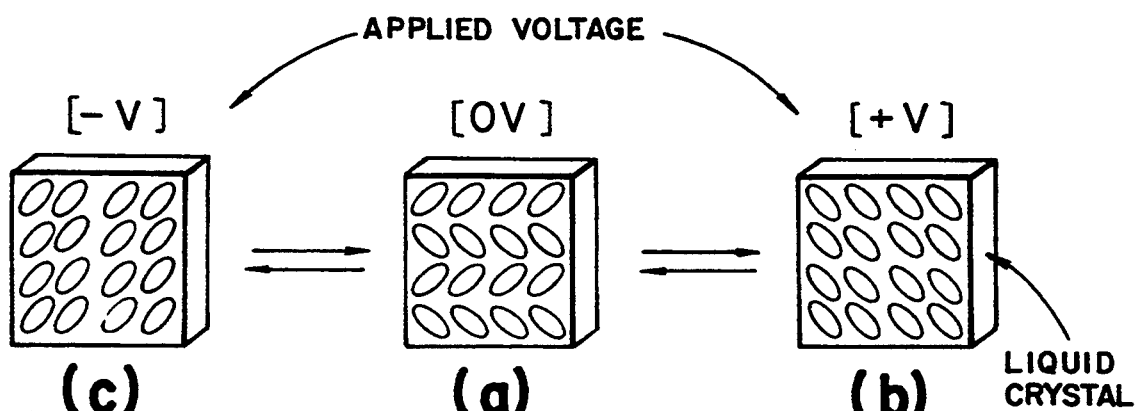
FIG. 3 shows the appearance of aligned "anti" ferroelectric liquid crystal molecules of the present invention in three stable states.
Figure 4:
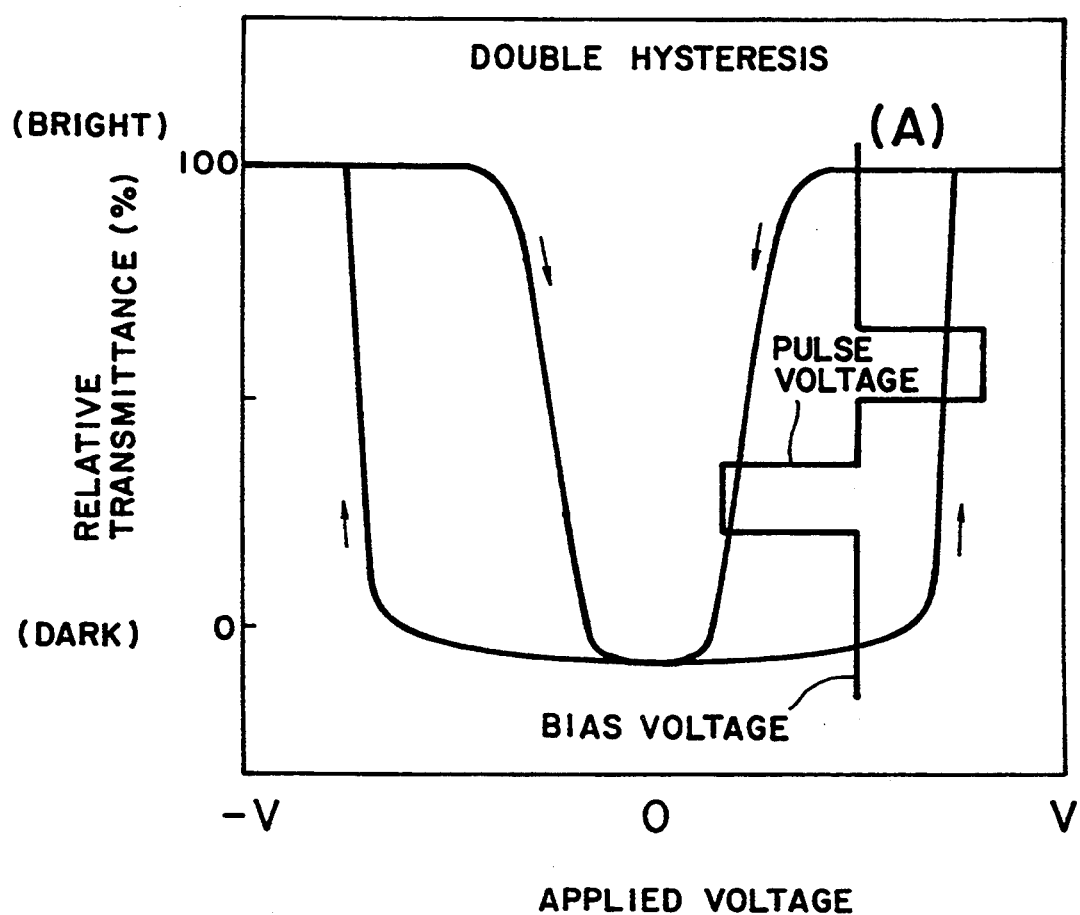
FIG. 4 is a graph showing characteristics of applied voltage-light transmittance indicating the fact that "anti" ferroelectric liquid crystal molecules change their light transmittance while drawing double hysteresis curves following to the applied voltage.

The present invention relates, first, to an antiferroelectric liquid crystal compound represented by the formula (I)

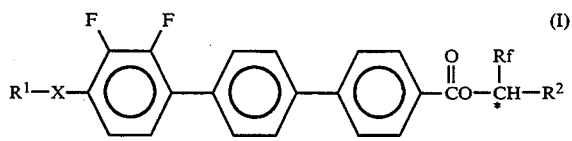

wherein $R^1$ and $R^2$ are independently selected from an alkyl group of $C_4$-$C_{18}$, respectively, Rf is $CF_3$ or $C_2F_5$, X is O, COO, or a single bond, and * shows an optically active carbon atom.

Preferable compounds in the first aspect of the present invention include antiferroelectric liquid crystal compounds represented by the following formulae (I-1) and (I-2):

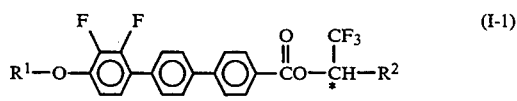

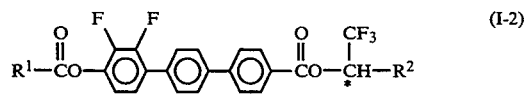

wherein $R^1$ and $R^2$ are the same as those in the formula (I) above.

The present invention relates, second, to an antiferroelectric liquid crystal compound represented by the formula (II)

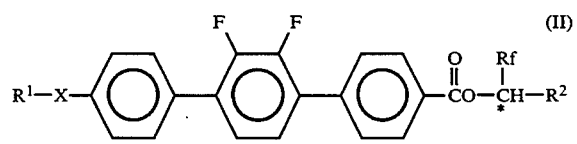

wherein $R^1$, $R^2$, Rf, X and * are the same as those in the formula (I).

Preferable compounds in the second aspect of the present invention include antiferroelectric liquid crystal compounds represented by the following formulae (II-1), (II-2), and (II-3):

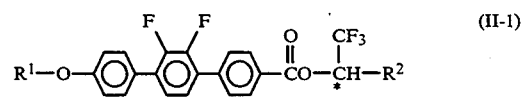

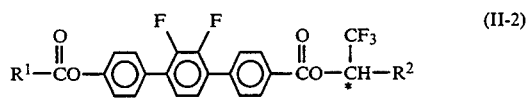

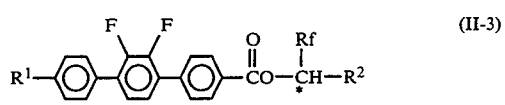

wherein $R^1$, $R^2$, and * are the same as those in the formula (I).

The present invention relates, third, to an antiferroelectric liquid crystal compound represented by the formula (III)

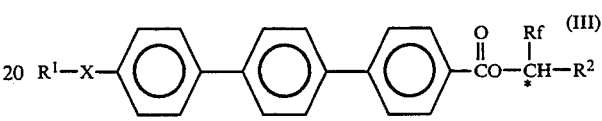

wherein $R^1$, $R^2$, Rf, X and * are the same as those in the formula (I).

Preferable compounds in the third aspect of the present invention include antiferroelectric liquid crystal compounds represented by the following formula (III-1)

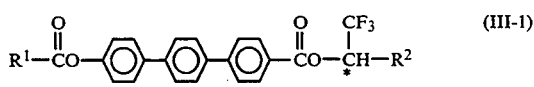

wherein $R^1$, $R^2$, and * are the same as those in the formula (I).

The compounds of the present invention can be produced by methods wherein known synthetic procedures disclosed in N. Miyaura et al. [Synth. Commun. 11, 513 (1981)] and others are used in combination.

The objective compound (7-1) in Synthesis Example 1 explained below can be prepared by subjecting 4-alkoxy-1-bromobenzene and 2,3-difluorophenyl boronic acid to a coupling reaction to form compound (1-1), converting the compound (1-1) to a lithium compound (2-1) and then to a boronic acid compound (3-1), subjecting the compound (3-1) to a coupling reaction with 4-bromobenzonitrile to form compound (4-1), subjecting the nitrile compound to hydrolysis to convert the nitrile group to carboxyl group to form compound (5-1), then converting the compound (5-1) to an acid chloride (6-1), and finally subjecting the compound (6-1) to esterification with an optically active alcohol such as 1,1,1-trifluoro-2-alkanol.

The compound (6-2) shown in Synthesis Example 2 can be prepared by using lithium-2,3-difluorobenzene as a starting material, subjecting it to an addition reaction of alkylaldehyde, dehydration reaction, and reduction reaction to form compound (1-2), converting the compound (1-2) to boronic acid compound (2-2), subjecting the compound (2-2) to a coupling reaction with 4-bromo-4'-cyanobiphenyl to form compound (3-2), subjecting the compound (3-2) to hydrolysis to convert the cyano group to carboxyl group to form compound (4-2), and then repeating the procedures similar to those in Synthesis Example 1.

Further, Synthesis Example 3 explains a method for producing another compound of the present invention wherein anhydrous aluminium chloride and acetyl chloride are reacted to a terphenyl to perform a Friedel-Crafts reaction to form compound (1-3). The Friedel-Crafts catalysts used in the reaction of Synthesis Example 3 include aluminium bromide (AlBr₃), iron trichloride (FeCl₃), tin tetrachloride (SnCl₄), and antimony pentachloride (SbCl₅) in addition to anhydrous aluminium chloride (AlCl₃).

Then, the compound (1-3) is subjected to a haloform reaction with a hypohalaous compound such as sodium hypobromide (NaOBr) and sodium hypochlorite (NaOCl) to oxidize acetyl group (CH₃CO) to carboxyl group (COOH) to form compound (2-3). The compound (2-3) is converted to an ethyl ester derivative (3-3) by a conventional method.

Further, Friedel-Crafts reaction mentioned above and then Baeyer-Villiger rearrangement are conducted to form compound (5-3) through compound (4-3). Next, hydrolysis is performed by using a base such as potassium hydroxide or sodium hydroxide to form compound (6-3). The hydroxyl group and carboxyl group in the compound (6-3) are converted to methoxymethyloxy group and ethyl ester group, respectively, to form compound (8-3) through compound (7-3).

Then, the ethyl ester group is converted back to carboxyl group by using a base such as potassium hydroxide to form compound (9-3), and the compound (9-3) is subjected to esterification by using an optically active 1,1,1-trifluoro-2-alkanol and a dehydration-condensation agent to form compound (10-3). The dehydration-condensation agent includes dicyclohexylcarbodiimide(DCC)-aminopyridine compounds, 2-chloro-1,3,5-trinitrobenzene and pyridine compounds, and N,N'-carbonyldiimidazole.

Then, the methoxymethyloxy group in the compound (10-3) is converted to hydroxyl group with an acid such as hydrogen chloride at an ambient temperature and then reacted with alkanoylchloride

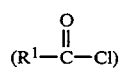

to produce the objective compound (12-3).

The same compound as the compound (12-3) can also be produced by methods wherein known synthetic procedures disclosed in N. Miyaura et al. [Synth. Commum. 11, 513 (1981)] and others are used in combination.

That is, in Synthesis Example 4, compound (1-4) is prepared by reacting 4-bromoanisole with triisopropylborate at a low temperature below −50° C. Then, the compound (1-4) is subjected to a coupling reaction with 4-bromo-4'-cyanobiphenyl to form compound (2-4). The compound (2-4) is subjected to hydrolysis in the presence of a base such as potassium hydroxide in a water-ethanol solution to convert the nitrile group to carboxyl group to prepare compound (3-4). The compound (3-4) is reacted with an acid to convert the methoxy group to hydroxyl group to form compound (4-4) and then the compound (4-4) is subjected to a reaction with alkanoylchloride (R¹COCl) to form compound (5-4).

Further, the compound (5-4) is converted to acid chloride (6-4) and the compound (6-4) is subjected to esterification with an optically active alcohol such as 1,1,1-trifluoro-2-alkanol to provide the objective compound (7-4).

SYNTHESIS EXAMPLE 1

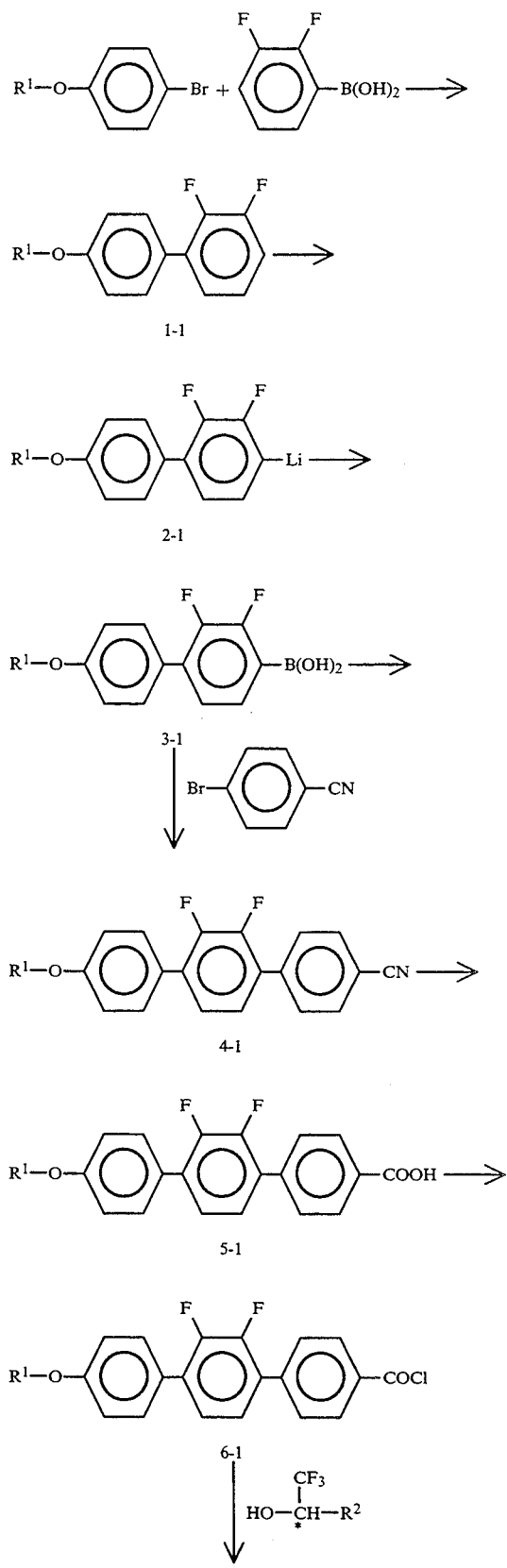

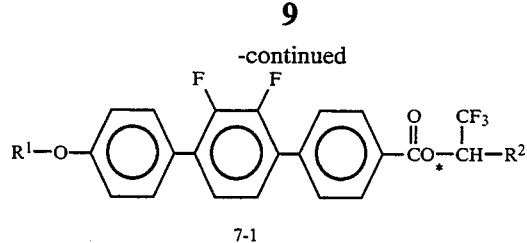
7-1
SYNTHESIS EXAMPLE 2
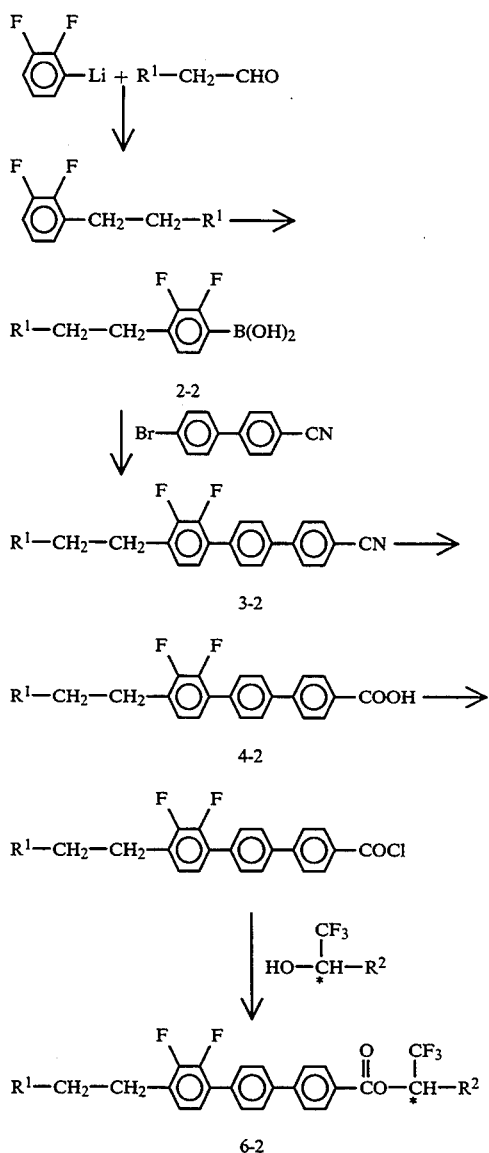
SYNTHESIS EXAMPLE 3
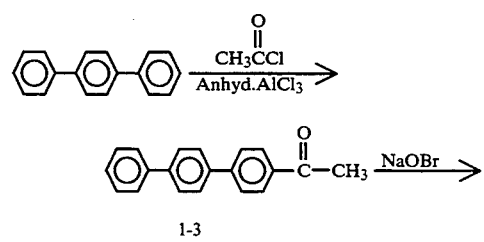
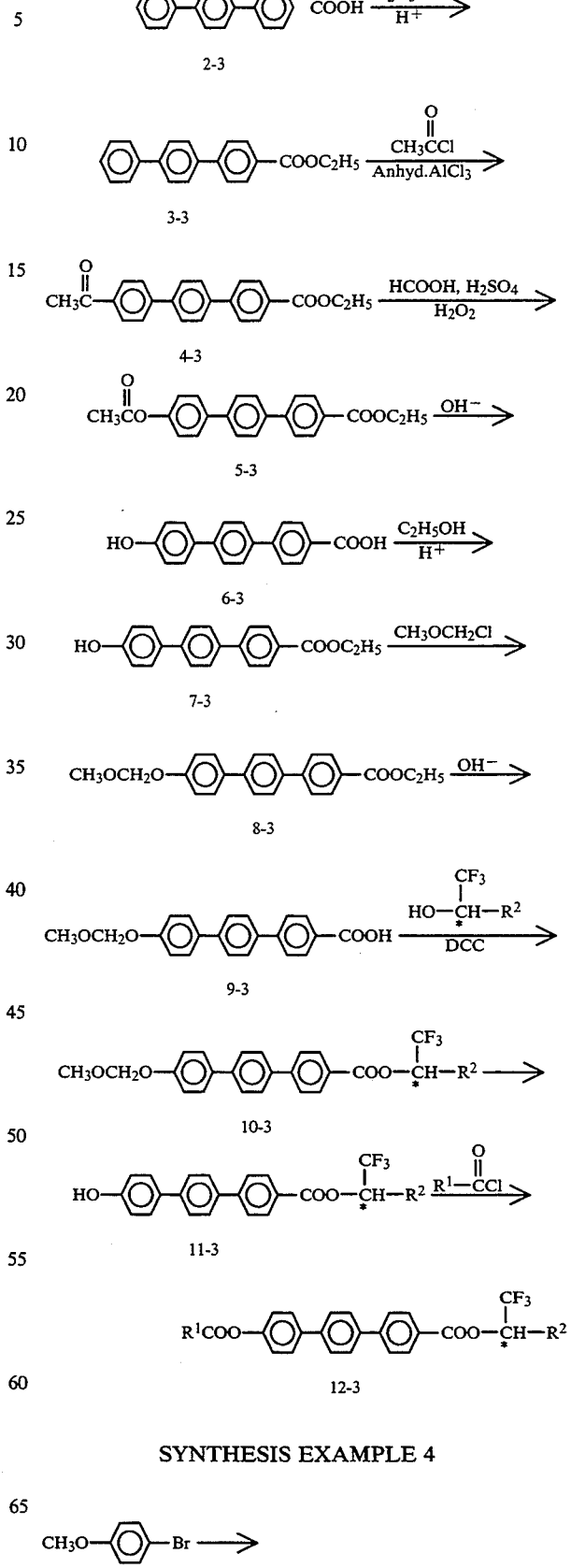
SYNTHESIS EXAMPLE 4

-continued

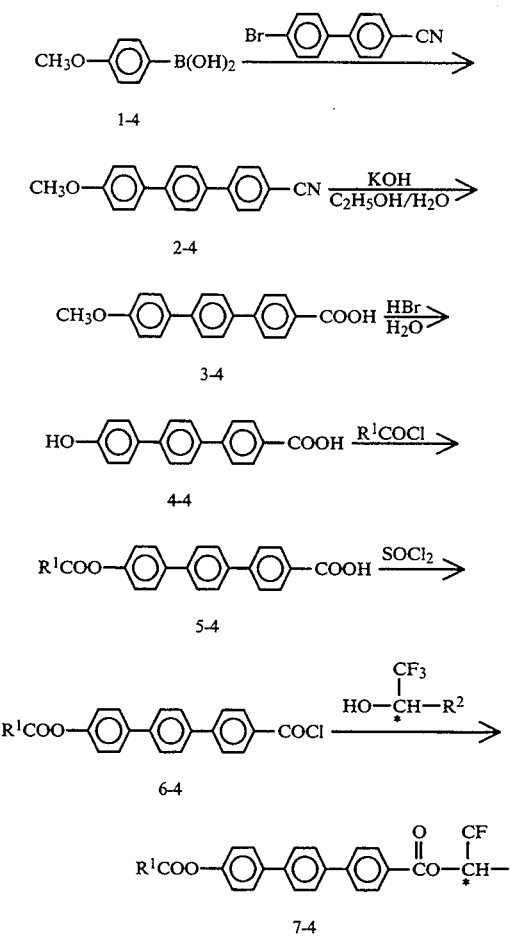

EXAMPLE

The present invention will now be described in further detail with reference to Examples and comparative Examples. However, it should be understood that the present invention is by no means restricted by such Specific Examples.

Example 1

4-n-octyloxy-2,3-difluoro-4''-(1,1,1-trifluoro-2-octyloxycarbonyl)-p-terphenyl

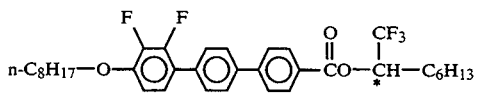

[1] Synthesis of

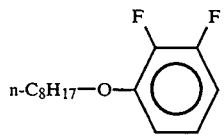

After 7.5 g of o-difluorobenzene was dissolved in 80 ml of dried tetrahydrofuran (THF), the solution thus formed was cooled down to −70° C. under a nitrogen atmosphere and then added dropwise with 42 ml of butyllithium (1.6 mol/liter hexane solution) at a temperature lower than −55° C. The solution was continuously stirred at the same temperature for 1.5 hours and added dropwise with a THF solution containing 24.8 g of triisopropylborate at a temperature of −65° C. to −60° C. After the dropping of the solution was finished, the solution was continuously stirred at an ambient temperature for 12 hours, added further with 60 ml of a 10% aqueous hydrochloric acid solution, and continuously stirred for 1 hour. The reaction mixture thus obtained was subjected to extraction with an ether, washed with water, dried, and subjected to distillation under a reduced pressure to separate the solvent to obtain 9.0 g of 2,3-difluorophenyl boronic acid.

The boronic acid in an amount of 9.0 g was dissolved in 60 ml of an ether, and the solution thus formed was added dropwise with 60 ml of a 10% aqueous hydrogen peroxide while being refluxed under a heated condition. After the dropping of the aqueous hydrogen peroxide was finished, the reflux under a heated condition was further continued for 2 hours. Then, the ether layer was separated with a separating funnel, washed with water, dried, and then subjected to distillation under a reduced pressure to separate the solvent to obtain 7.1 g of 2,3-difluorophenol.

After 7.1 g of 2,3-difluorophenol was dissolved in 100 ml of acetone, the solution thus formed was added with 17 g of potassium carbonate (K$_2$CO$_3$) and 12.0 g of n-octylbromide, heated to reflux for 8 hours, and then subjected to distillation under a reduced pressure to separate acetone. The residue was added with 100 ml of an ether and subjected to extraction. The insoluble materials were separated by filtration, washed with a 10% aqueous sodium hydroxide solution and water in turn. The solvent was separated by distillation under a reduced pressure to obtain 15 g of a product. The product was purified by a silica gel column chromatography to obtain 12.1 g of 2,3-difluoro-1-n-octyloxybenzene.

[2] Synthesis of

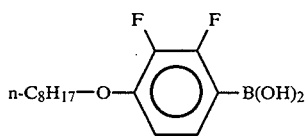

After 12.1 g of the compound synthesized in [1] above was dissolved in 60 ml of a dried THF, the solution thus formed was cooled down to −70° C., added dropwise with 32 ml of butyllithium, and continuously stirred at the same temperature for 2 hours. Then, the solution was added dropwise with a THF solution containing 18.8 g of triisopropylborate at a temperature of lower than −60° C. and continuously stirred at an ambient temperature for 12 hours. Then, the solution was further added with 60 ml of a 10% aqueous hydrochloric acid solution and continuously stirred for 1 hour. The reaction mixture thus formed was subjected to extraction with an ether, washed with water, dried, and subjected to distillation under a reduced pressure to separate the solvent to obtain 13.2 g of 4-n-octyloxy-2,3-difluorophenyl boronic acid.

[3] Synthesis of

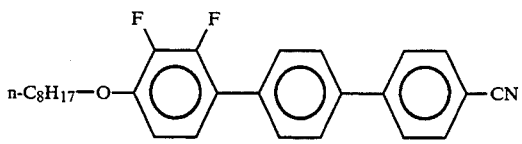

To 15 ml of ethanol was added 3.69 g of the 4-n-octyloxy-2,3-difluorophenyl boronic acid obtained in [2] above to prepare a solution (A). The solution (A) was added to a mixture of 2.58 g of 4-bromo-4'-cyanobiphenyl, 400 mg of tetrakis(triphenylphosphine)-palladium(0), 36 ml of benzene, and 36 ml of an aqueous sodium carbonate ($Na_2CO_3$) solution (2 mol/liter). After the solution thus formed was stirred for 12 hours while being heated, the solution was cooled down to 5° C., and the crystals thus precipitated were separated by filtration. The crystals thus obtained were dissolved in a mixed solvents of n-hexane and ethyl acetate (10:2), subjected to purification with a silica gel column chromatography, recrystallized from methylene chloride-hexane to obtain 2.95 g of 4-n-octyloxy-2,3-difluoro-4''-cyano-p-terphenyl.

[4] Synthesis of

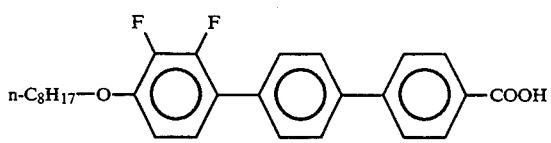

A mixture of 2.46 g of the terphenyl compound obtained in [3] above, 250 ml of ethanol, and 9 g of potassium hydroxide was stirred for 72 hours while being heated, added further with 10 g of acetic acid, and continuously stirred for 2 hours while being heated. The solution was cooled to precipitate crystals, and the crystals thus precipitated were separated by filtration, washed with water, and dried to obtain 2.38 g of 4-n-octyloxy-2,3-difluoro-4''-carboxyl-p-terphenyl.

[5] Synthesis of

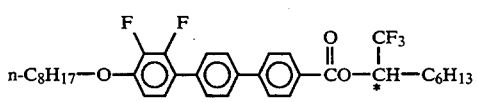

A mixture of 2.35 g of the terphenyl compound obtained in [4] above, 20 ml of methylene chloride, 3 ml of thionyl chloride ($SOCl_2$), and few drops of dimethyl formamide (DMF) was heated at 40° C. for 2 hours. After the solvents were separated by distillation, the compound was dissolved in 30 ml of methylene chloride. The solution thus formed was added dropwise to 30 ml of methylene chloride solution containing 1.04 g of (R)-1,1,1-trifluoro-2-octanol, 0.69 g of dimethylaminopyridine (DMAP), and 0.58 g of triethylamine. After the dropping of the methylene chloride solution was finished, the resulting solution was continuously stirred at an ambient temperature for 4 hours. The reaction liquid thus obtained was washed with a diluted aqueous hydrochloric acid solution and water in turn, subjected to distillation to separate the solvent. The residue thus obtained was subjected to purification by a silica gel column chromatography using a mixed solvents of n-hexane and ethyl acetate (10:1) and by recrystallization to obtain 1.70 g of 4-n-octyloxy-2,3-difluoro-4''-(1,1,1-trifluoro-2-octyloxycarbonyl)-p-terphenyl.

The phase transition temperatures (° C.) of the terphenyl compound thus prepared observed with a microscope equipped with a hot stage were as follows:

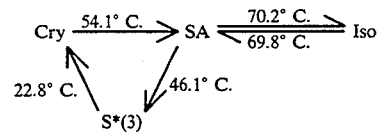

(The microscope used in Example 1 was also used for the determination of phase transition temperature in the following all Examples and Comparative Examples.)

Example 2

4-n-nonyloxy-2,3-difluoro-4''-(1,1,1-trifluoro-2-octyloxycarbonyl)-p-terphenyl

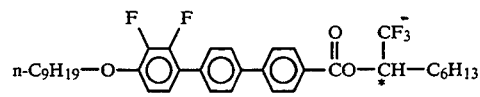

Example 1 was repeated except that 12.2 g of n-nonylbromide was used instead of n-octylbromide in [1] in Example 1.

The phase transition temperatures (° C.) of the terphenyl compound obtained were as follows:

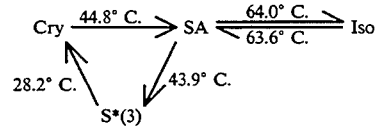

Example 3

4-n-decyloxy-2,3-difluoro-4''-(1,1,1-trifluoro-2-octyloxycarbonyl)-p-terphenyl

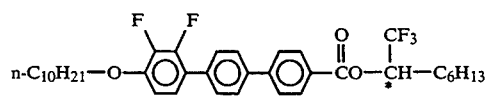

Example 1 was repeated except that 12.4 g of n-decylbromide was used instead of n-octylbromide in [1] in Example 1.

The phase transition temperatures (° C.) of the terphenyl compound obtained were as follows:

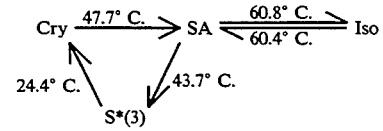

Example 4

4-n-octyloxy-2,', 3'-difluoro-4''-(1,1,1-trifluoro-2-octyloxycarbonyl)-p-terphenyl

[1] Synthesis of

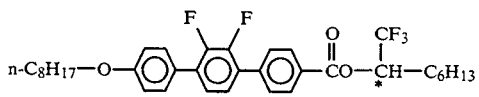

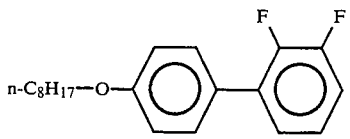

In 100 ml of acetone, 8.0 g of 4-bromophenol, 8.9 g of n-octylbromide, and 13 g of potassium carbonate were heated to reflux for 12 hours. After the solvent was distilled off under a reduced pressure, the residue thus obtained was extracted with isopropyl ether, washed with a 5% aqueous sodium hydroxide solution and water in turn. The ether was distilled off, and the residue was purified by a silica gel column chromatography using a mixed solvents of n-hexane and diethyl ether (10:1) and subjected to distillation to obtain 8.4 g of 4-bromo-1-n-octyloxybenzene.

To a mixture of 4.2 g of the 4-bromo-1-n-octyloxybenzene, 0.5 g of tetrakis(triphenylphosphine) palladium(0), 53 ml of benzene, and 53 ml of an aqueous sodium carbonate solution (2 mol/liter), 26 ml of ethanol containing 3.0 g of 2,3-difluorophenyl boronic acid synthesized by the same method as in [1] in Example 1 was added dropwise, and then the solution thus formed was heated to reflux for 5 hours. After the solution was cooled, it was added with 200 ml of an ether to extract the product, washed with water and dried. The solvent was distilled off under a reduced pressure. The residue thus obtained was purified by a silica gel column chromatography using a mixed solvents of n-hexane and diethyl ether (10:2) to obtain 2.8 g of 4-n-octyloxy-2', 3'-difluorobiphenyl.

[2] Synthesis of

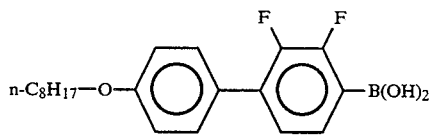

After 2.72 g of the 4-n-octyloxy-2', 3'-difluorobiphenyl was dissolved in 20 ml of a dried THF, the solution thus formed was cooled down to −70° C. under a nitrogen atmosphere and added dropwise with 5.5 ml of butyllithium (1.6 mol/liter hexane solution). The solution was continuously stirred at the same temperature for 2 hours, and then added dropwise with a THF solution containing 3.21 g of triisopropylborate. After the solution was stirred at an ambient temperature for 12 hours, it was added with 7.7 ml of a 10% aqueous hydrochloric acid solution and further stirred for 1 hour. Then, the same after-treatments as in [1] in Example 1 were repeated to obtain 2.27 g of 4-(p-n-octyloxyphenyl)-2,3-difluorobenzene boronic acid.

[3] Synthesis of

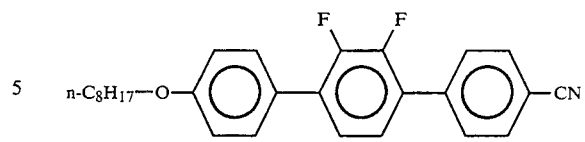

The boronic acid compound obtained in [2] above in an amount of 2.26 g and 1.09 g of 4-bromobenzonitrile were subjected to the same procedures as in [3] in Example 1 to obtain 2.15 g of 4-n-octyloxy-2', 3'-difluoro-4''-cyano-p-terphenyl.

[4] Synthesis of

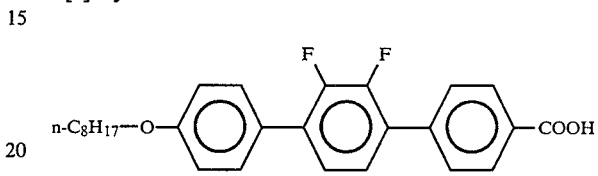

The procedures in [4] in Example 1 were repeated by using 2.15 g of the compound prepared in [3] above as a raw material to obtain 1.88 g of 4-n-octyloxy-2', 3'-difluoro-4''-carboxyl-p-terphenyl.

[5] Synthesis of

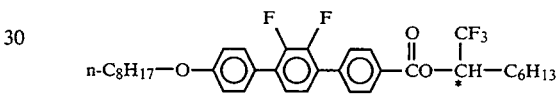

The procedures in [5] in Example 1 were repeated by using 1.88 g of 4-n-octyloxy-2', 3'-difluoro-4''-carboxyl-p-terphenyl prepared in [4] above to obtain 1.64 g of 4-n-octyloxy-2', 3'-difluoro-4''-(1,1,1-trifluoro-2-octyloxycarbonyl)-p-terphenyl. The terphnyl compound thus obtained was subjected to recrystallization from an anhydrous ethanol and used for the determination of phase transition temperature.

The phase transition temperature (° C.) of the recrystallized terphenyl compound were as follows:

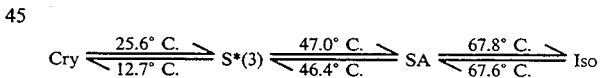

Example 5

4-n-nonyloxy-2', 3'-difluoro-4''-(1,1,1-trifluoro-2-octyloxycarbonyl)-p-terphenyl

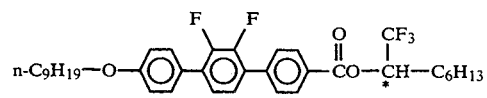

Example 4 was repeated except that 13 g of n-nonylbromide was used instead of n-octylbromide in [1] in Example 4.

The phase transition temperature (° C.) of the terphenyl compound thus obtained were as follows:

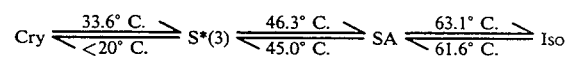

Example 6

4-n-decyloxy-2',  3'-difluoro-4"-(1,1,1-trifluoro-2-octyloxycarbonyl)-p-terphenyl

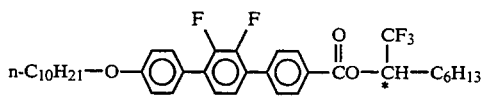

Example 4 was repeated except that 14 g of n-decylbromide was used instead of n-octylbromide in [1] in Example 4.

The phase transition temperature (° C.) of the terphenyl compound thus obtained were as follows:

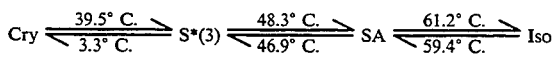

Comparative Example 1

4-n-octyloxy-3-fluoro-4"-(1,1,1-trifluoro-2-octyloxycarbonyl)p-terphenyl

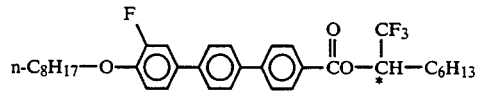

[1] Synthesis of

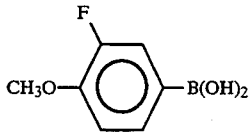

To 50 ml of carbon disulfide in which 50 g of o-fluoroanisole was dissolved, a solution prepared by mixing 27 g of carbon dislufide with 63.8 g of bromine was slowly added dropwise at a temperature of −5° C. to 5° C. in 1 hour with stirring. After the dropping of the solution was finished, it was further stirred at 5° C. for 30 min, added with 125 ml of water, and subjected to extraction with chloroform. The chloroform layer was washed with an aqueous sodium thiosulfate ($Na_2S_2O_3$) solution and an aqueous sodium hydrogencarbonate ($NaHCO_3$) solution in turn. Then, the solvent was distilled off with an evaporator under a reduced pressure to obtain 70.9 of 4-bromo-2-fluoroanisole.

Then, 9.6 g of magnesium was added to 230 ml of THF, and the solution thus formed was slowly added dropwise with 70.9 g of the 4-bromo-2-fluoroanisole obtained by the procedure mentioned above to prepare a Grignard reagent. The reagent was added dropwise to a mixture of 123.8 g of triisopropyl borate and 391 ml of THF at a temperature of −60° C. to −50° C. with stirring. After the dropping of the reagent was finished, the solution was subjected to reaction at an ambient temperature for 2 hours, added with 242 ml of a 1N-aqueous hydrochloric acid solution, subjected to further reaction for 1 hour, extracted with an ether, washed with water, and concentrated under a reduced pressure to obtain 46.2 g of 4-methoxy-3-fluorobenzene boronic acid.

[2] Synthesis of

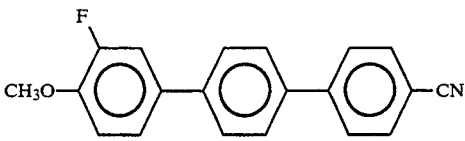

To a mixture of 2.4 g of 4-bromo-4'-cyanobiphenyl, 0.37 g of tetrakis(triphenylphosphine)palladium(0), 15.2 ml of a 2N aqueous sodium carbonate solution, and 19.4 ml of benzene, a solution which was prepared by dissolving 1.9 g of 4-methoxy-3-fluoro-benzene boronic acid synthesized in [1] above in 14.4 ml of ethanol was slowly added dropwise with stirring, and the solution was subjected to reflux for 8 hours. After the reflux was finished, the solution was cooled, and the crystals thus precipitated were separated by filtration and washed with water and methanol in turn, and dried to obtain 2.5 g of 4-methoxy-3-fluoro-4"-cyano-p-terphenyl.

[3] Synthesis of

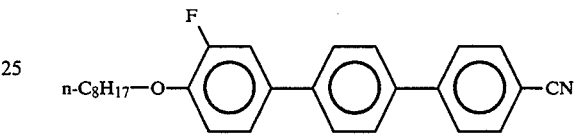

The 4-methoxy-3-fluoro-4"-cyano-p-terphenyl in an amount of 2.5 g obtained in [2] above was added with 200 ml of methylene chloride, and added slowly dropwise with stirring with a solution which was prepared by dissolving 8 g of boron tribromide ($BBr_3$) in 50 ml of methylene chloride, and the solution was subjected to reaction at an ambient temperature overnight. The solution was dispersed in 200 ml of water and extracted with THF. After the solvent was distilled off under a reduced pressure, the residual crystals were subjected to recrystallization from a mixed solvents of THF-methanol (10:1) to obtain 2.2 g of 4-hydroxy-3-fluoro-4"-cyano-p-terphenyl.

Then, a mixture of 1 g of the 4-hydroxy-3-fluoro-4"-cyano-p-terphenyl thus obtained, 0.77 g of n-octylbromide, 0.55 g of potassium carbonate, and 10 ml of dimethyl formamide was subjected to reaction at 100° C. for 1 hour with stirring. After the reaction was finished, the solution was dispersed in 50 ml of water, subjected to extraction with ethyl acetate, washed with water, and subjected to distillation to separate the solvent under a reduced pressure to obtain solid materials. The solid materials were recrystallyzed from methanol to obtain 1.23 g of the objective compound.

[4] Synthesis of

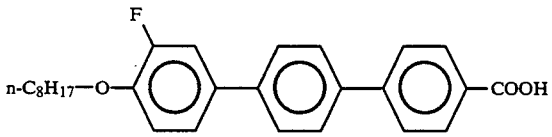

A mixture of 1,23 g of 4-n-octyloxy-3-fluoro-4"-cyano-p-terphenyl, 4.5 g of potassium hydroxide powders, and 123 ml of ethanol was refluxed for 72 hours with stirring, added with 4.7 g of acetic acid, and further refluxed for 2 hours. After the reflux was finished, the solution was cooled to precipitate crystals. The crystals thus precipitated were separated by filtration, washed with water, and dried to obtain 1.2 g of 4-n-octyloxy-3-fluoro-4″-carboxyl-p-terphenyl.

[5] Synthesis of

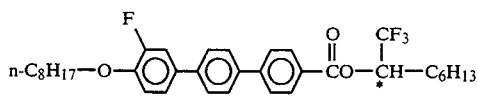

A mixture of 1.2 g of the 4-n-octyloxy-3-fluoro-4″-carboxyl-p-terphenyl obtained in [4] above, 0.8 g of thionyl chloride, 20 ml of methylene chloride, and a catalytic amount of dimethyl formamide was subjected to reflux at 40° C. for 2 hours. After the reflux was finished, the solution was concentrated under a reduced pressure, and then subjected several times to azeotropic distillation with toluene to separate unreacted thionyl chloride to obtain acid chloride materials.

Then, 20 ml of methylene chloride solution containing the acid chloride materials mentioned above was slowly added dropwise, while being cooled with an ice water, to a mixed solution of 0.45 g of (R)-(+)-1,1,1-trifluoro-2-octanol [α] $D^{20}$=+25.6 (C=0.9960, in $CHCl_3$), 0.3 g of dimethylaminopyridine (DMAP), 0.26 g of triethylamine, and 20 ml of methylene chloride. The solution was further subjected to reaction at an ambient temperature overnight. The reaction solution thus obtained was washed with a diluted aqueous hydrochloric acid solution and water in turn, the solvent was distilled off, and the residue was subjected to purification by a silica gel column chromatography using a mixed solvents of n-hexane and ethyl acetate (10:1) and by recrystallization from ethanol to obtain 1.7 g of 4-n-octyloxy-3-fluoro-4″-(1,1,1-trifluoro-2-octyloxycarbonyl)-p-terphenyl. The terphenyl compound was further purified by recrystallization from an anhydrous ethanol for the determination of phase transition temperature.

The phase transition temperature (° C.) of the recrystallized terphenyl compound were as follows:

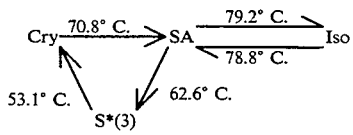

Comparative Example 2

4-n-nonyloxy-3-fluoro-4″-(1,1,1-trifluoro-2-octyloxycarbonyl)-p-terphenyl

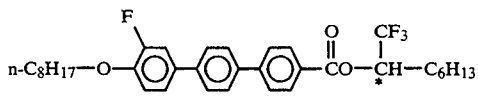

Comparative Example 1 was repeated except that 0.78 g of n-nonylbromide was used instead of n-octylbromide in [3] in Comparative Example 1.

The phase transition temperature (° C.) of the terphenyl compound thus obtained were as follows:

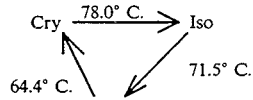

Comparative Example 3

4-n-decyloxy-3-fluoro-4″-(1,1,1-trifluoro-2-octyloxycarbonyl)-p-terphenyl

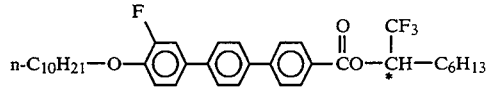

Comparative Example 1 was repeated except that 0.79 g of n-decylbromide was used instead of n-octylbromide in [3] in Comparative Example 1.

The phase transition temperature (° C.) of the terphenyl compound thus obtained were as follows:

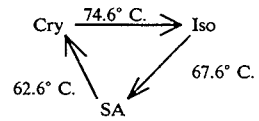

Comparative Example 4

4-n-octyloxy-4″-(1,1,1-trifluoro-2-octyloxycarbonyl)-p-terphenyl

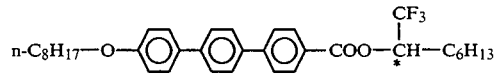

After 1.6 g of 4-n-octyloxyterphenyl-4″-carboxylic acid was heated with an excess amount of thionyl chloride under reflux condition for 6 hours, unreacted thionyl chloride was distilled off to obtain 4-n-octyloxyterphenyl-4″-carboxylic acid chloride.

To a solution prepared by dissolving the acid chloride mentioned above in 50 ml of methylene chloride, another solution prepared by dissolving 0.7 g of 1,1,1-trifluoro-2-octanol, 0.4 g of triethylamine, and 0.1 g of dimethylaminopyridine in 50 ml of methylene chloride was slowly added while being cooled with ice, and the solution thus formed was subjected to reaction at an ambient temperature overnight.

Then, the reaction liquid thus obtained was put in an ice water and extracted with methylene chloride. The methylene chloride layer was washed with a diluted aqueous hydrochloric acid solution, water, aqueous sodium carbonate solution, and water in turn, dried with anhydrous sodium sulfate, and subjected to distillation to separate the solvent to obtain a crude product. The crude product was purified by a silica gel column chromatography using a mixed solvents of n-hexane and ethyl acetate (10:1) to obtain 1.1 g of the objective optically active compound. The compound was further purified by recrystallization from anhydrous ethanol for the determination of phase transition temperature.

The phase transition temperature (° C.) of the recrystallized compound were as follows:

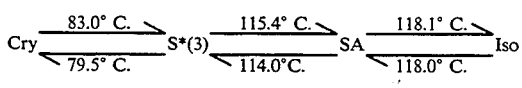

Comparative Example 5

4-n-octyloxy-4″-(1,1,1-trifluoro-2-decyloxycarbonyl-p-terphenyl

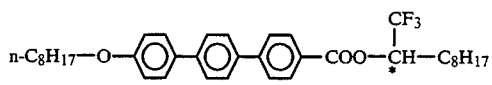

Comparative Example 4 was repeated except that 0.7 g of 1,1,1-trifluoro-2-decanol was used instead of 1,1,1-trifluoro-2-octanol to obtain the objective compound.

The phase transition temperature (° C.) of the compound thus obtained were as follows:

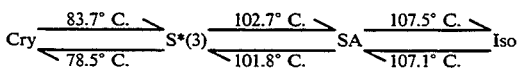

Example 7

4-n-octylcarbonyloxy-4″-(1,1,1-trifluoro-2-octyloxycarbonyl)-p-terphenyl

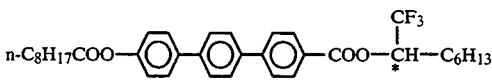

Synthesis of the objective compound was performed in the order as follows:

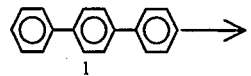
1

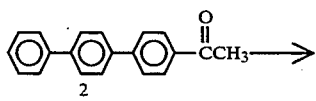
2

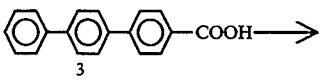
3

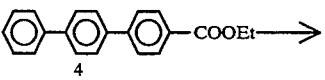
4

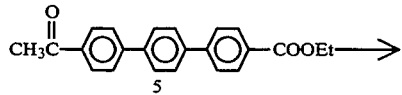
5

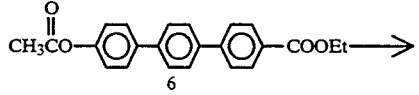
6

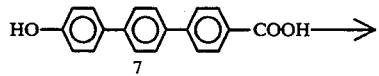
7

-continued

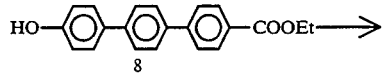
8

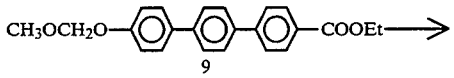
9

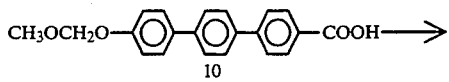
10

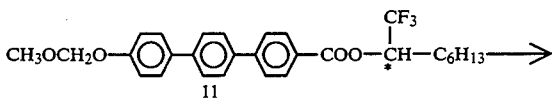
11

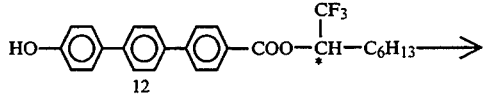
12

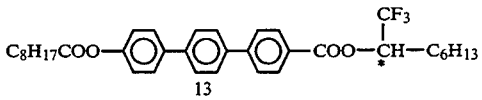
13

Synthesis of Compound 2:

After a mixture of 172 g of terphenyl, 860 ml of benzene, and 353 g of acetyl chloride was cooled to −5° C., it was added with a total of 200 g of anhydrous aluminium chloride in few instalments, and subjected to reaction at −5° C. for 1 hour and further at 10° C. for 1 hour. The solid materials thus formed were separated by filtration, washed with a total of 4 liter of methanol in few instalments, and then recrystallized from chloroform to obtain 121 g of 4-acetyl-p-terphenyl, 2. The yield was 59%.

Synthesis of Compound 3:

After 50 g of the 4-acetyl-p-terphenyl obtained in the synthesis of compound 2 above was dissolved in 2 liter of dioxane, the solution thus formed was added with an aqueous sodium hypobromite solution (prepared from 151 g of bromine ($Br_2$) and 780 g of a 20% aqueous sodium hydroxide solution) and subjected to reaction at 60° C. for 2 hours. After the solution was cooled down to a room temperature, it was added with an aqueous hydrochloric acid solution to make it acidic. The crystals thus precipitated were separated by filtration, washed with water, added in 3 liter of THF, and heated to dissolve. After the insoluble materials were separated by filtration, the filtrate was concentrated to 500 ml, and the crystals thus precipitated were separated by filtration to obtain 44 g 4-carboxyl-p-terphenyl, 3. The yield was 88%.

Synthesis of Compound 4:

After 44 g of the 4-carboxyl-p-terphenyl obtained in the synthesis of compound 3 was heated to reflux with 450 ml of chloroform and 450 ml of thionyl chloride for 4 hours, the solvent and thionyl chloride were distilled off under a reduced pressure. The residue was added with 3 liter of a 3% triethylamine ethanol solution, and heated for 12 hours with stirring. After the solvent was distilled off under a reduced pressure, it was added with 2 liter of THF. The insoluble materials were separated by filtration, the filtrate was subjected to distillation under a reduced pressure to precipitate crystals, and the crystals were washed with benzene to obtain 35 g of 4-carboxyl-p-terphenyl ethyl ester, 4. The yield was 71%.

Synthesis of Compound 5:

After 29.2 g of the ester obtained in the synthesis of compound 4 above was dissolved in 290 ml of methylene chloride, it was added with 30.9 g of anhydrous aluminium chloride, added dropwise with 18.3 g of acetyl chloride, and then subjected to reaction by heating to reflux for 4 hours. The reaction liquid thus obtained was dispersed in an ice water, extracted with chloroform, washed with water, dried, and then subjected to distillation under a reduced pressure to separate the solvent. The residue was recrystallized from a mixed solvents of chloroform and methanol to obtain 24.1 g of 4-acetyl-4″-carboxyl-p-terphenyl ethyl ester, 5. The yield was 72%.

Synthesis of Compound 6:

After 27.0 g of the ester obtained in the synthesis of compound 5 above was dissolved in 540 ml of methylene chloride, it was added with 121 g of formic acid, 46 g of anhydrous acetic acid, and 15 g of a concentrated sulfuric acid, and then added dropwise with a 35% aqueous hydrogen peroxide while being cooled with ice. After the solution was heated under reflux condition for 8 hours, the solution was dispersed in an ice water, extracted with chloroform, washed with water, dried, and subjected to distillation under a reduced pressure to separate the solvent. The residue was recrystallized from a mixed solvents of chloroform and methanol to obtain 16.5 g of 4-acetyloxy-4″-carboxyl-p-terphenyl ethyl ester, 6. The yield was 58%.

Synthesis of Compound 7:

After 16.5 g of the compound obtained in the synthesis of compound 6 above was dissolved in 500 ml of ethanol, it was added with 34 g of a 50% aqueous potassium hydroxide solution, and refluxed for 5 hours. The solution was added with an aqueous hydrochloric acid solution to adjust its pH to 1 and further refluxed for 1 hour. The solution was cooled down to a room temperature to precipitate crystals, and the crystals thus precipitated were separated by filtration, washed with water, and dried to obtain 12.5 g of 4-hydroxy-4″-carboxyl-p-terphenyl, 7. The yield was 94%.

Synthesis of Compound 8:

After a mixture of 25.0 g of the compound obtained in the synthesis of compound 7 above, 1 liter of ethanol, 1 liter of THF, and 100 g of a concentrated sulfuric acid was heated for 3 hours with stirring, the insoluble materials were separated by filtration while being heated. The filtrate was allowed to stand to cool, and the crystals thus precipitated were separated by filtration, washed with water, and dried to obtain 23.1 g of 4-hydroxy-4″-carboxyl-p-terphenyl ethyl ester, 8. The yield was 85%.

Synthesis of Compound 9:

The ethyl ester obtained in the synthesis of compound 8 above in an amount of 13.7 g, 13.0 g of chloromethyl methyl ether, and 22.2 g of anhydrous potassium carbonate were heated at 100° C. in 70 ml of dimethyl formamide for 24 hours with stirring. After the solution thus formed was cooled, it was added with 500 ml of water, and the crystals thus precipitated were separated by filtration. The crystals were dissolved in 600 ml of THF, the insoluble materials were separated by filtration, and the solution was subjected to distillation under a reduced pressure to separate the solvent. The residue was added with methanol, and the crystals thus precipitated were separated by filtration, and dried to obtain 10.1 g of 4-methoxymethyloxy-4″-carboxyl-p-terphenyl ethyl ester, 9. The yield was 64%.

Synthesis of Compound 10:

The compound obtained in the synthesis of compound 9 above in a amount of 22.8 g, 950 ml of ethanol, and 64 g of a 50% aqueous potassium hydroxide solution were heated to reflux for 4 hours. The reaction mixture thus obtained was added with a diluted aqueous hydrochloric acid solution to adjust its pH to 3 to 4, and the crystals thus precipitated were separated by filtration, washed with water, and dried to obtain 21.0 g of 4-methoxymethyloxy-4″-carboxyl-p-terphenyl, 10. The yield was 100%.

Synthesis of Compound 11:

After 11.1 g of the compound obtained in the synthesis of compound 10 above was dissolved in 200 ml of methylene chloride, it was added with 7.0 g of (R)-(+)-1,1,1-trifluoro-2-octanol, 50 mg of dimethylaminopyridine, and 7.0 g of ethylene dichloride EDC.HCl, and stirred at an ambient temperature for 24 hours. The reaction liquid thus obtained was washed with water, dried, and subjected to distillation under a reduced pressure to separate the solvent. The residue was purified by a silica gel column chromatography and further recrystallized from methanol to obtain 8.0 g of 4-methoxymethyloxy-4″-(1,1,1-trifluoro-2-octyloxycarbonyl)-p-terphenyl, 11. The yield was 48%.

Synthesis of Compound 12:

After 8.0 g of the compound obtained in the synthesis of compound 11 above was dissolved in 110 ml of acetone, it was added with 17 ml of a concentrated hydrochloric acid solution and stirred at an ambient temperature for 2 hours. The reaction liquid thus obtained was added with 300 ml of water, and cooled with ice. The crystals thus precipitated were separated by filtration. After the crystals were washed with a 10% hydrate acetone, they were dried to obtain 6.5 g of 4-hydroxy-4″-(1,1,1-trifluoro-2-octyloxycarbonyl)-p-terphenyl, 12. The yield was 89%.

Synthesis of Compound 13:

After 2.0 g of the compound obtained in the synthesis of compound 12 above was dissolved in 20 ml of methylene chloride, it was added with 0.54 g of triethylamine, and added dropwise with 1.0 g of nonanoylchloride. The solution was stirred at an ambient temperature for 12 hours, washed with a diluted aqueous hydrochloric acid solution, saturated salt water, saturated aqueous sodium bicarbonate solution, and salt water in turn, dried, and subjected to distillation under a reduced pressure to separate the solvent. The crude product thus obtained was purified first by a silica gel column chromatography, next by an ODS flash chromatogrphy, and then by recrystallization from ethanol to obtain 1.2 g of 4-n-octylcarbonyloxy-4″-(1,1,1-trifluoro-2-octyloxycarbonyl)-p-terphenyl, 13. The compound was further purified by recrystallization from anhydrous ethanol for the determination of phase transition temperature. The yield was 46%.

The phase transition temperature (° C.) of the finally purified compound were as follows:

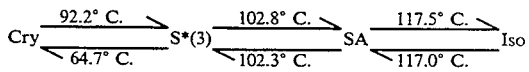

Example 8

4-n-nonylcarbonyloxy-4″-(1,1,1-trifluoro-2-octyloxycarbonyl)-p-terphenyl

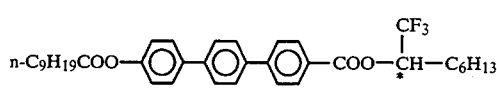

Example 7 was repeated except that 1.0 g of decanoylchloride was used as a raw material instead of 1.0 g of nonanoylchloride in the synthesis of compound 13 in Example 7 to obtain 1.1 g of the objective compound. The compound was further purified by recrystallization from anhydrous ethanol for the determination of phase transition temperature.

The phase transition temperature (° C.) of the recrystallized compound were as follows:

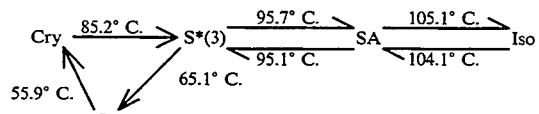

Sx: Highly ordered smectic phase.

Example 9

4-n-decylcarbonyloxy-4″-(1,1,1-trifluoro-2-octyloxycarbonyl)-p-terphenyl

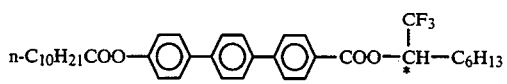

Example 7 was repeated except that 1.1 g of undecanoyl was used as a raw material instead of 1 g of nonanoylchloride in the synthesis of compound 13 in Example 7 to obtain 1.2 g of the objective compound. The compound was further purified by recrystallization from anhydrous ethanol for the determination of phase transition temperature.

The phase transition temperature (° C.) of the recrystallized compound were as follows:

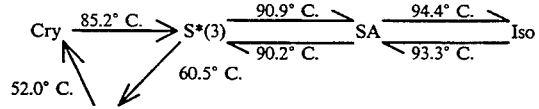

Example 10

4-n-octylcarbonyloxy-4″-(1,1,1-trifluoro-2-decyloxycarbonyl)-p-terphenyl

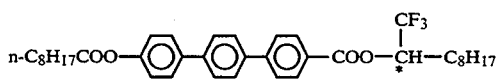

Example 7 was repeated except that 7.0 g of (R)-(+)-1,1,1-trifluoro-2-decanol was used instead of (R)-(+)-1,1,1-trifluoro-2-octanol used in the synthesis of the compound 11 in Example 7 to obtain 1.1 g of the objective compound. The compound was further purified by recrystallization from anhydrous ethanol for the determination of phase transition temperature.

The phase transition temperature (° C.) of the recrystallized compound were as follows:

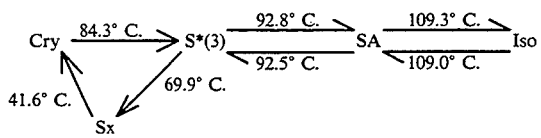

Example 11

4-n-nonylcarbonyloxy-4″-(1,1,1-trifluoro-2-decyloxycarbonyl)-p-terphenyl

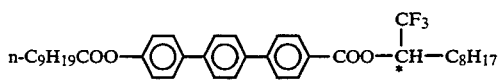

Example 10 was repeated except that 1.0 g of decanoylchloride was used instead of 1.0 g of nonanoylchloride to obtain 1.1 g of the objective compound. The compound was further purified by recrystallization from anhydrous ethanol for the determination of phase transition temperature.

The phase transition temperature (° C.) of the recrystallized compound were as follows:

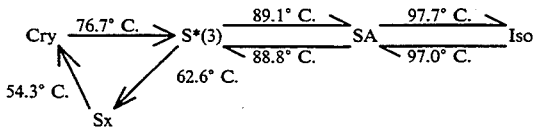

Example 12

4-n-carbonyloxy-4″-(1,1,1-trifluoro-2-decyloxycarbonyl)-p-terphenyl

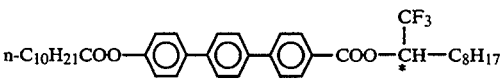

Example 10 was repeated except that 1.2 g of undecanoylchloride was used instead of 1.0 g of nonanoylchloride to obtain 1.2 g of the objective compound. The compound was further purified by recrystallization from anhydrous ethanol for the determination of phase transition temperature.

The phase transition temperature (° C.) of the recrystallized compound were as follows:

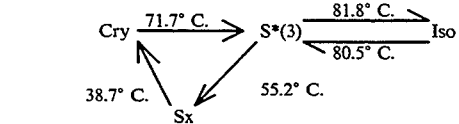

Example 13

The liquid crystal compound obtained in Example 4 was filled in the form of an isotropic phase to a liquid crystal cell having a cell thickness of 1.9 μm and having a rubbed polyimide oriented film on an ITO electrode substrate to prepare a liquid crystal thin film cell.

The liquid crystal cell thus prepared was arranged on a polarizing microscope equipped with a photomultiplier where 2 polarizing plates were orthogonally arranged with each other in such a state that the visual field is dark when voltage is 0 V.

Figure 5A:
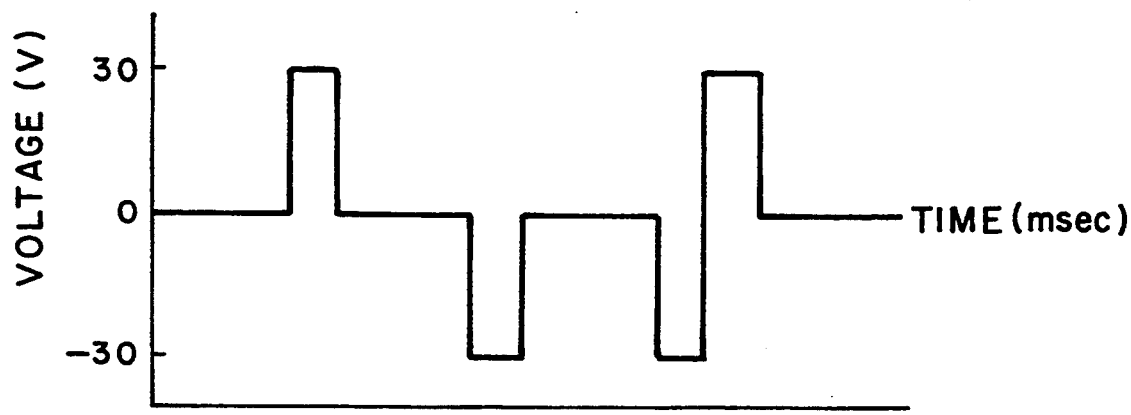
FIG. 5(a) shows relationship between a pulse voltage and a response time.

The liquid crystal cell was slowly cooled down to temperature, $T_{CA}$ (° C.) where phase $S^*_{(3)}$ appeared. Then, the liquid crystal cell was further cooled down slowly to temperatures lower than the $T_{CA}$ (° C.) and a pulse voltage as shown in FIG. 5(A) was applied at the temperatures.

Figure 5B:
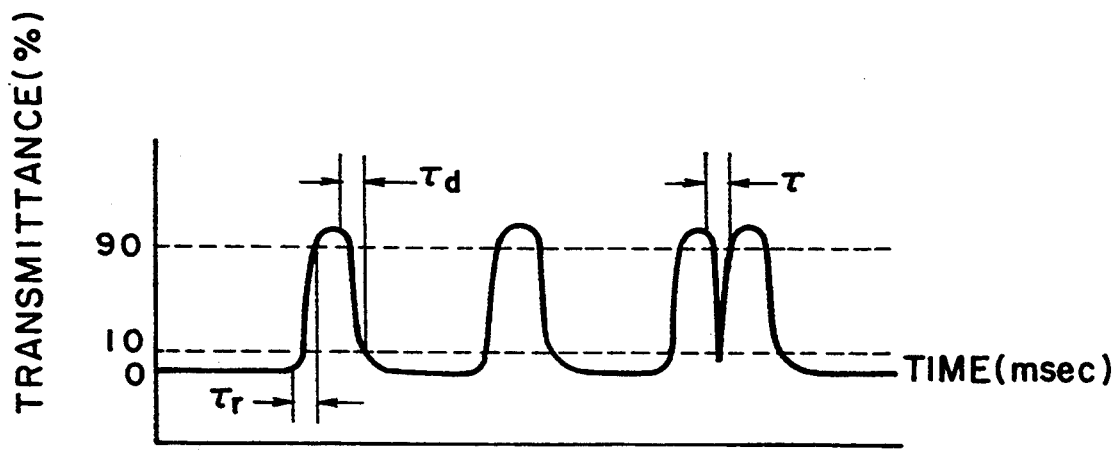
FIG. 5(B) shows the relationship between the transmittance responding to the pulse voltage in FIG. 5(A) and the response time $\tau$, $\tau_r$, $\tau_d$.
Figure 6:
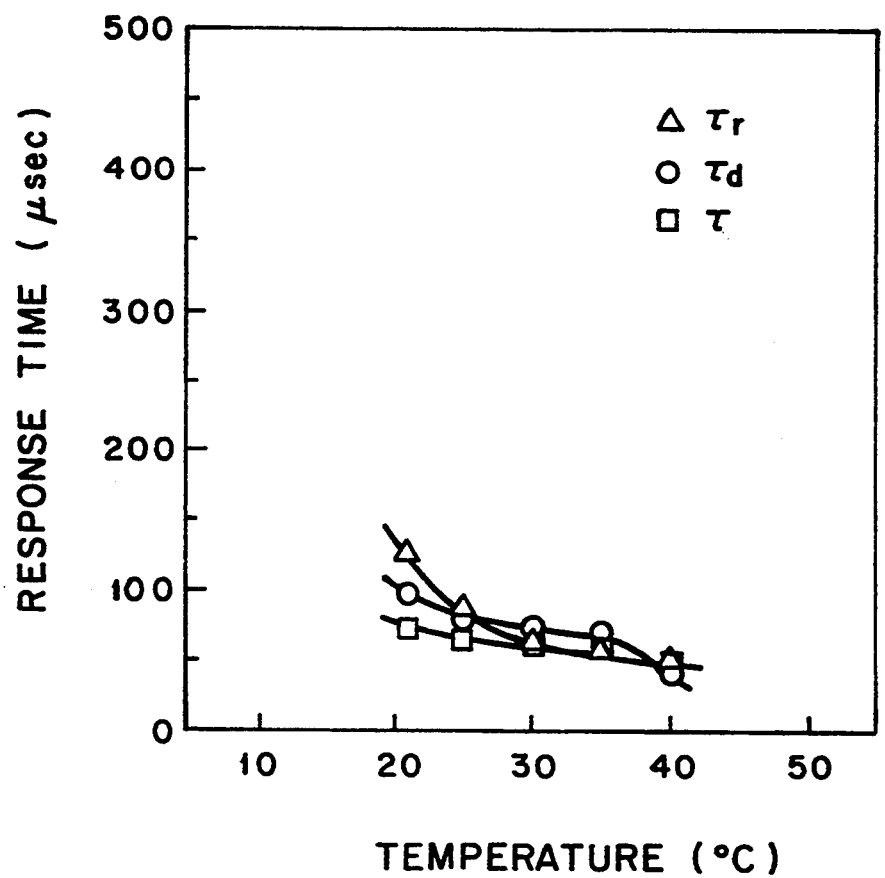
FIGS. 6 and 7 are graphs showing the relationship between the response time and temperature obtained in Examples 13 and 14, respectively.

The response times, $\tau_r$, $\tau_d$, and $\tau$ which were obtained from the change in the transmittance (%) as shown in FIG. 5(B) are shown in FIG. 6.

Definition of the response times will be understood from the following:

The response time $\tau_r$ for the transition from the first stable state (dark state) to the second stable state (bright state), the response time $\tau_d$ for the transition from the second stable state (bright state) to the first stable state (dark state), and response time $\tau$ for the transition from the second stable state (bright state) to the third stable state (bright state) through the first stable state were measured. Smaller response times, $\tau_r$, $\tau_d$, and $\tau$ to electric field means a desirable more rapid response.

Example 14

Example 13 was repeated except that the compound obtained in Example 7 was used instead of the compound obtained in Example 4.

Figure 7:
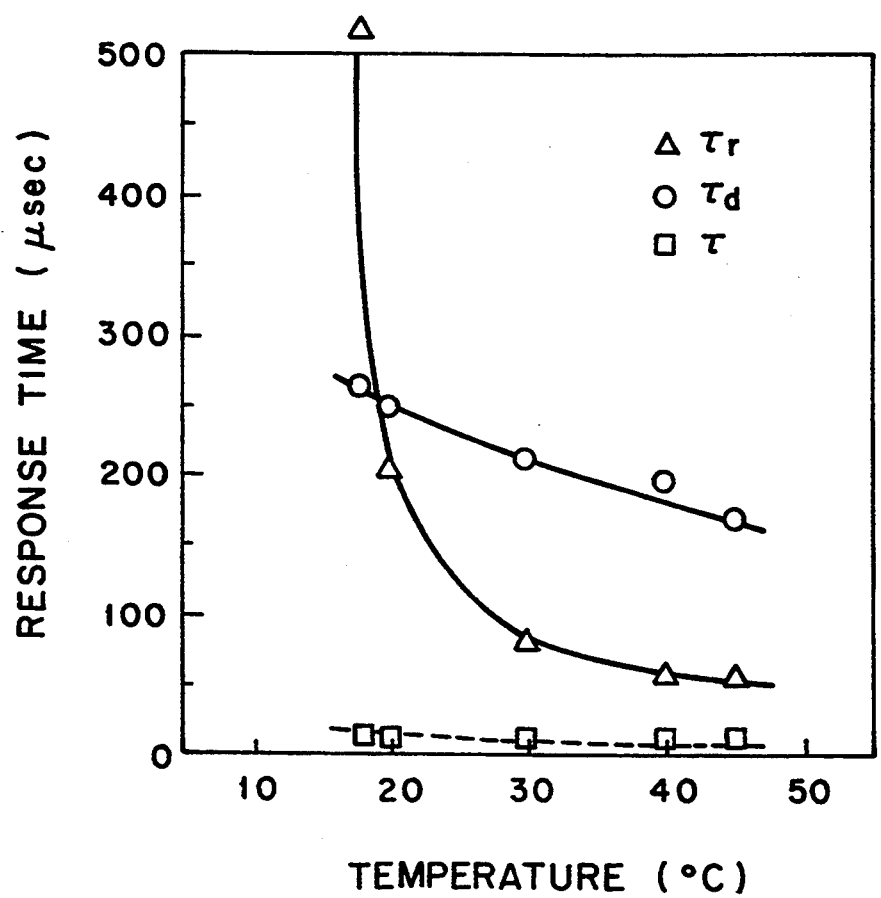

The response times measured are shown in FIG. 7.

Example 15

The liquid crystal cell having the same structure as that in Example 14 wherein the liquid crystal compound obtained in Example 7 was used was slowly cooled down at a temperature gradient of 0.1° to 1.0° C./min to the temperature, $T_{CA}$ (° C.) where the $S^*_{(3)}$ appeared. Then, the liquid crystal cell was further cooled down slowly to temperatures lower than the $T_{CA}$ (° C.) and a pulse voltage as shown in FIG. 5A was applied.

Figure 8:
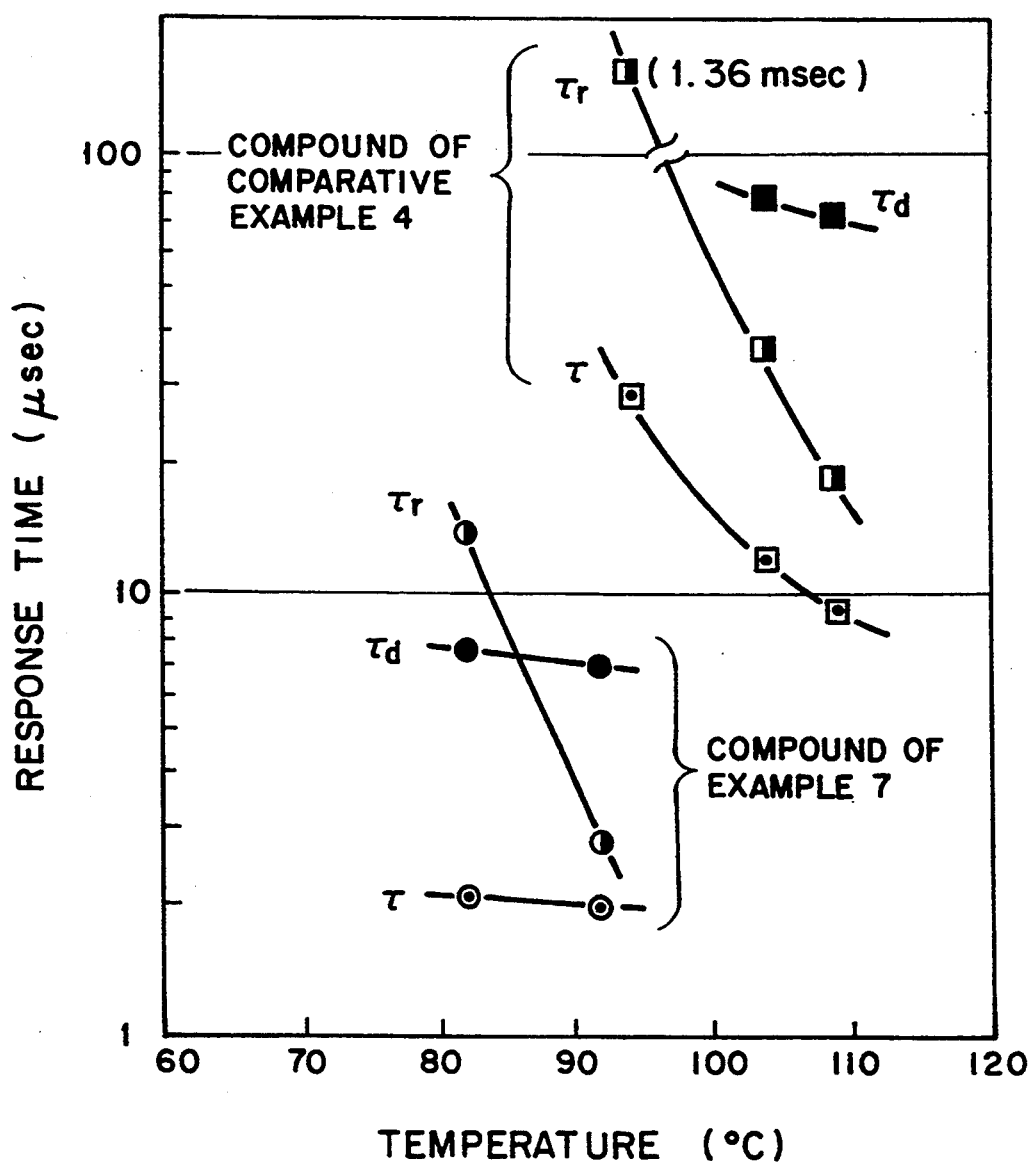
FIGS. 8 and 9 are graphs showing the relationship between the response time and temperature obtained in Example 15 and 16, and Comparative Example 6, respectively.

The response times, $\tau_r$, $\tau_d$, and $\tau$ which were obtained from the change in the transmittance (%) as shown in FIG. 5B are shown in FIG. 8.

Example 16

Example 15 was repeated except that the liquid crystal compound obtained in Example 10 was used instead of the liquid crystal compound obtained in Example 7.

Figure 9:
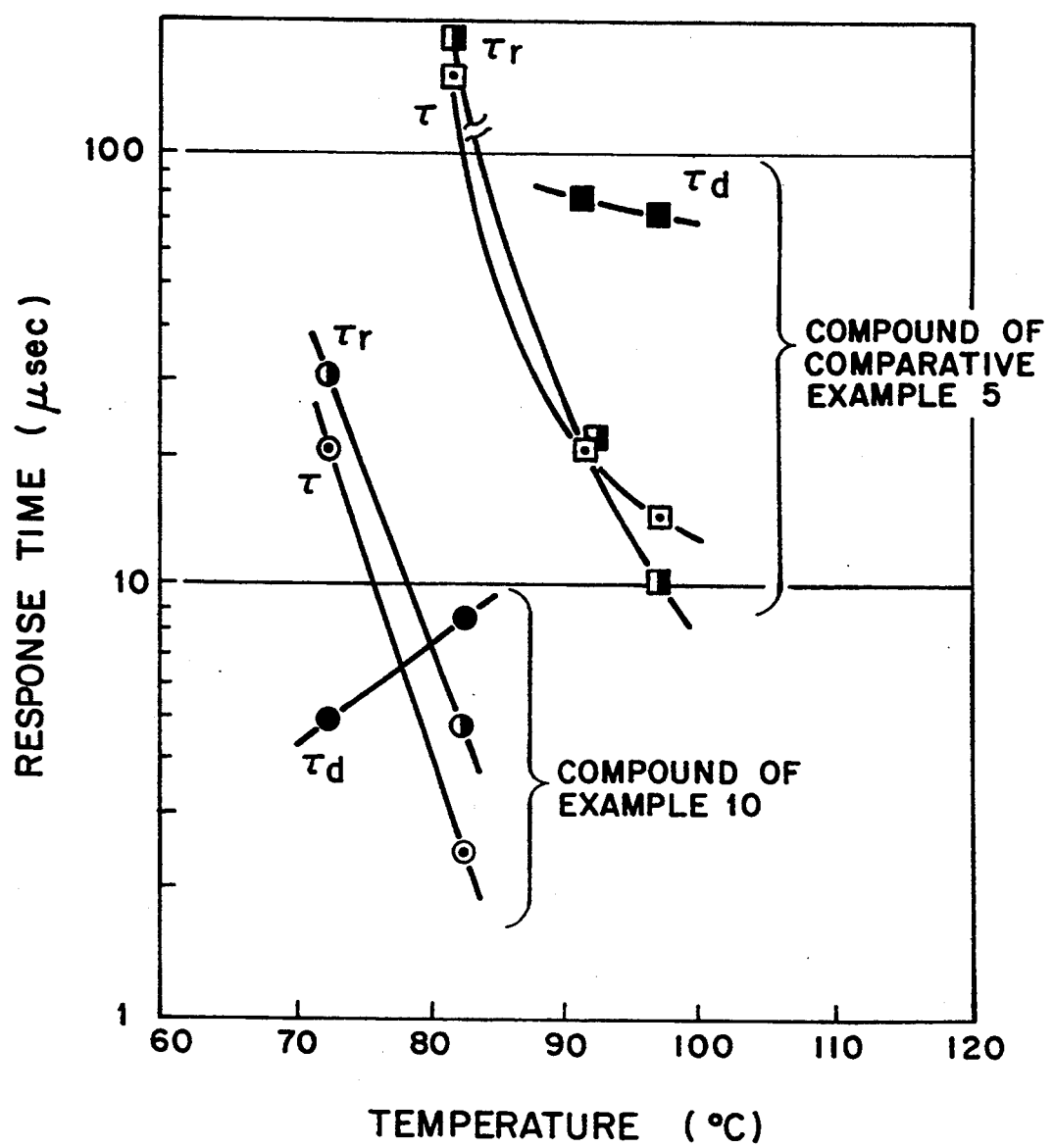

The response times measured are shown in FIG. 9.

Comparative Example 6

Example 15 was repeated except that the liquid crystal compounds obtained in comparative Examples 4 and 5, respectively, were used instead of the liquid crystal compound obtained in Example 7.

The response times measured are also shown in FIGS. 8 and 9, respectively.

We claim:

1. An antiferroelectric liquid crystal compound of formula (I):

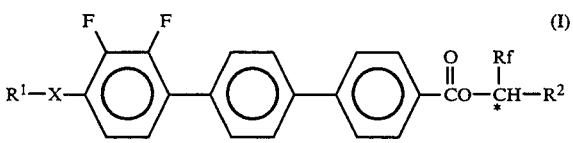

wherein $R^1$ and $R^2$ each is an alkyl group of $C_4$-$C_{18}$, Rf is $CF_3$ or $C_2F_5$, X is O, COO, or a single bond, and * shows an optically active carbon atom.

2. The antiferroelectric liquid crystal compound according to claim 1, wherein the compound of the formula (I) is represented by the following formula (I-1):

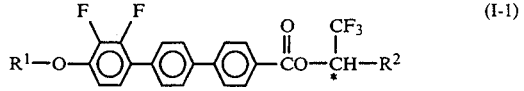

3. The antiferroelectric liquid crystal compound according to claim 1, wherein the compound of the formula (I) is represented by the following formula (I-2):

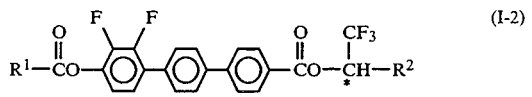

4. An antiferroelectric crystal compound of the formula (II):

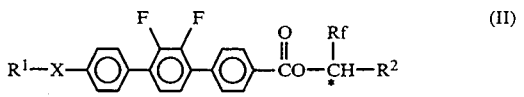

wherein $R^1$ and $R^2$ each is an alkyl group of $C_4$-$C_{18}$, Rf is $CF_3$ or $C_2F_5$, X is O, COO or a single bond, and * shows an optically active carbon atom.

5. The antiferroelectric liquid crystal compound according to claim 4, wherein the compound of the formula (II) is represented by the following formula (II-1):

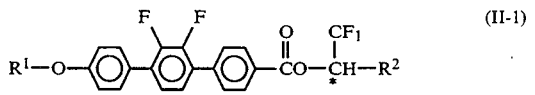

6. The antiferroelectric liquid crystal compound according to claim 4, wherein the compound of the formula (II) is represented by the following formula (II-2):

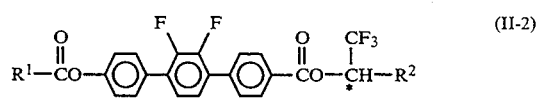

7. An antiferroelectric liquid crystal compound according to claim 1 or 4, wherein Rf is trifluoromethyl.

8. An antiferroelectric liquid crystal compound according to claim 1 or 4, wherein Rf is a pentafluoroethyl group.

9. An antiferroelectric liquid crystal compound according to claim 1 or 4, wherein X is —O—.

10. An antiferroelectric liquid crystal compound according to claim 1 or 4, wherein X is —COO—.

11. An antiferroelectric liquid crystal compound according to claim 1, wherein $R^1$ is a n-alkyl group selected from the group consisting $n$-$C_8H_{17}$ and $n$-$C_9H_{19}$.

12. An antiferroelectric liquid crystal compound according to claim 4, wherein $R_1$ is an $n$-$C_{10}H_{21}$ group.

13. An antiferroelectric liquid crystal compound according to claim 1 or 4, wherein $R^1$ is an alkyl group having six carbon atoms.

* * * * *